(12) United States Patent
Kaskoun et al.

(10) Patent No.: US 9,202,705 B1
(45) Date of Patent: Dec. 1, 2015

(54) INTEGRATED CIRCUIT MODULE WITH LEAD FRAME MICRO-NEEDLES

(71) Applicant: QUALCOMM Incorporated, San Diego, CA (US)

(72) Inventors: Kenneth Kaskoun, La Jolla, CA (US); Rongtian Zhang, San Diego, CA (US); Matthew Michael Nowak, San Diego, CA (US); Shiqun Gu, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 14/824,345

(22) Filed: Aug. 12, 2015

Related U.S. Application Data

(62) Division of application No. 14/326,842, filed on Jul. 9, 2014, now Pat. No. 9,138,191.

(51) Int. Cl.
| | |
|---|---|
| *H01L 21/44* | (2006.01) |
| *H01L 21/48* | (2006.01) |
| *H01L 21/306* | (2006.01) |
| *H01L 23/495* | (2006.01) |

(52) U.S. Cl.
CPC ........ *H01L 21/306* (2013.01); *H01L 23/49548* (2013.01)

(58) Field of Classification Search
CPC .............. H01L 21/565; H01L 21/4842; H01L 23/49548
USPC .................... 438/123, 124, 127; 257/E23.048
See application file for complete search history.

(56) References Cited

U.S. PATENT DOCUMENTS

| | | | | |
|---|---|---|---|---|
| 5,665,653 | A | * | 9/1997 | Bare .................... G01N 27/414 264/272.17 |
| 6,365,424 | B1 | * | 4/2002 | Bauer .................. G01D 11/245 257/690 |
| 6,727,579 | B1 | | 4/2004 | Eldridge et al. |
| 7,785,301 | B2 | | 8/2010 | Yuzhakov |

(Continued)

FOREIGN PATENT DOCUMENTS

WO 2013058879 A2 4/2013

OTHER PUBLICATIONS

Glucovation, "Glucose sensing for you", 2014, retrieved from URL: http://www.glucovation.com/whatCGM.html, 2 Pages.

(Continued)

*Primary Examiner* — Nitin Parekh
(74) *Attorney, Agent, or Firm* — The Marbury Law Group, PLLC

(57) ABSTRACT

An integrated circuit (IC) module with a lead frame micro-needle for a medical device, and methods of forming the IC module are described. The methods include forming a lead frame blank including a micro-needle integrally formed therein. The micro-needle may be bent beyond an initial lower side of the lead frame blank. The initial lower side may be joined with a protection layer such that the bent micro-needle is embedded in the protection layer, which may be removably attached to the initial lower side and the bent micro-needle. An IC component may be affixed to an upper side of the lead frame blank. The IC component and an upper surface of a core of the lead frame blank may be encapsulated with a molding compound forming a packaging of the IC module. Removal of the protection layer may expose the bent micro-needle projecting away from the packaging.

10 Claims, 9 Drawing Sheets

(56) References Cited

U.S. PATENT DOCUMENTS

| | | |
|---|---|---|
| 8,108,023 B2 | 1/2012 | Mir et al. |
| 8,187,183 B2 | 5/2012 | Jin et al. |
| 8,622,903 B2 | 1/2014 | Jin et al. |
| 8,736,037 B2 | 5/2014 | Powell et al. |
| 2007/0182008 A1 | 8/2007 | Hauenstein |
| 2008/0138583 A1 | 6/2008 | Bhandari et al. |
| 2010/0224970 A1* | 9/2010 | Powell .............. H01L 21/4832 257/676 |
| 2012/0012365 A1 | 1/2012 | Cherian et al. |
| 2013/0137950 A1 | 5/2013 | Harttig et al. |
| 2013/0321426 A1 | 12/2013 | Kamath et al. |
| 2013/0324824 A1 | 12/2013 | Kamath et al. |
| 2014/0367865 A1 | 12/2014 | Powell et al. |
| 2015/0015249 A1* | 1/2015 | Ausserlechner ....... G01R 15/20 324/252 |

OTHER PUBLICATIONS

Rodon T., et al., "The Effect of Common Sterilization Techniques on The Mechanical Properties of DuPont Performance Polymers Special Control (SC) and Premium Control (PC) Grades," Du Pont de Nemours Intl., Jul. 2010, pp. 1-26.

Sandia National Laboratories: "Diagnostic medical lab on a patch," Biomedical sensor array, R&D Magazine, 2007, pp. 1-5.

* cited by examiner

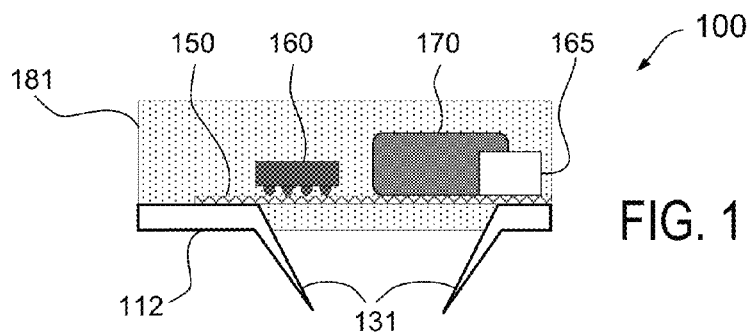
FIG. 1
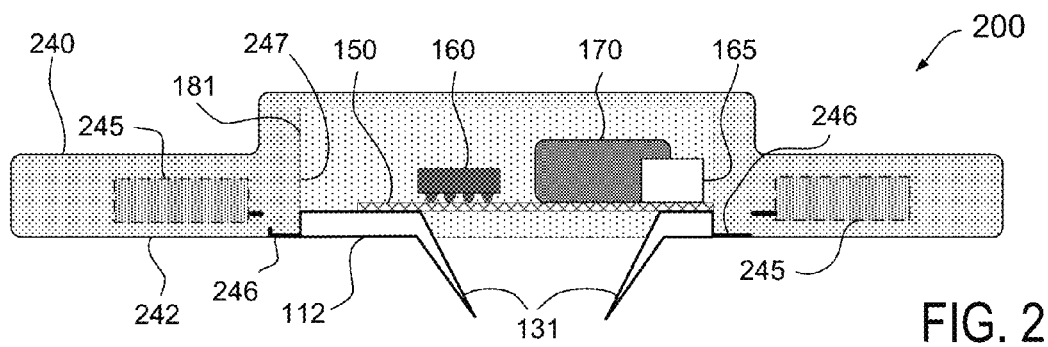
FIG. 2
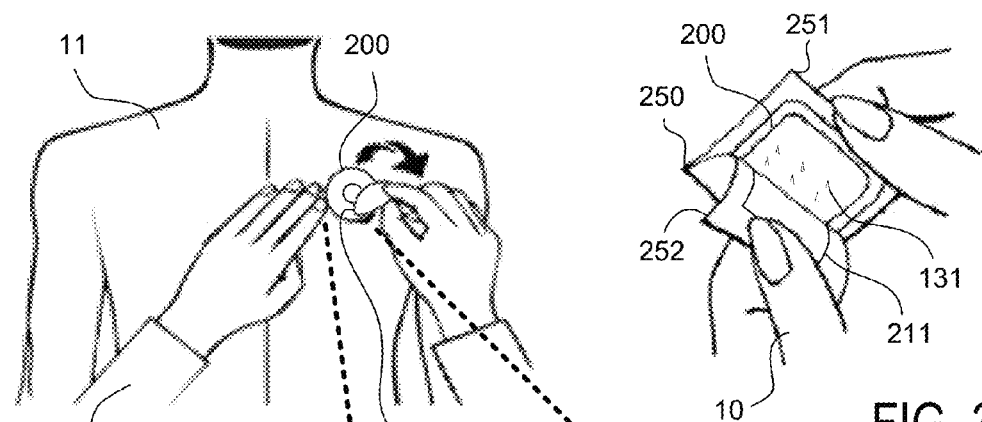
FIG. 3A
FIG. 3B
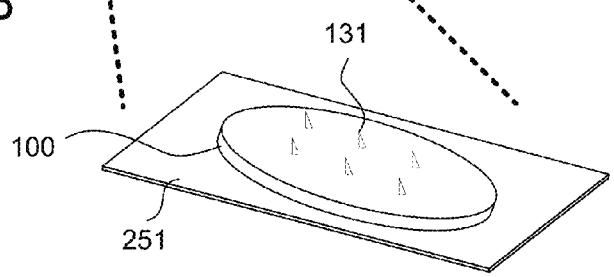
FIG. 3C

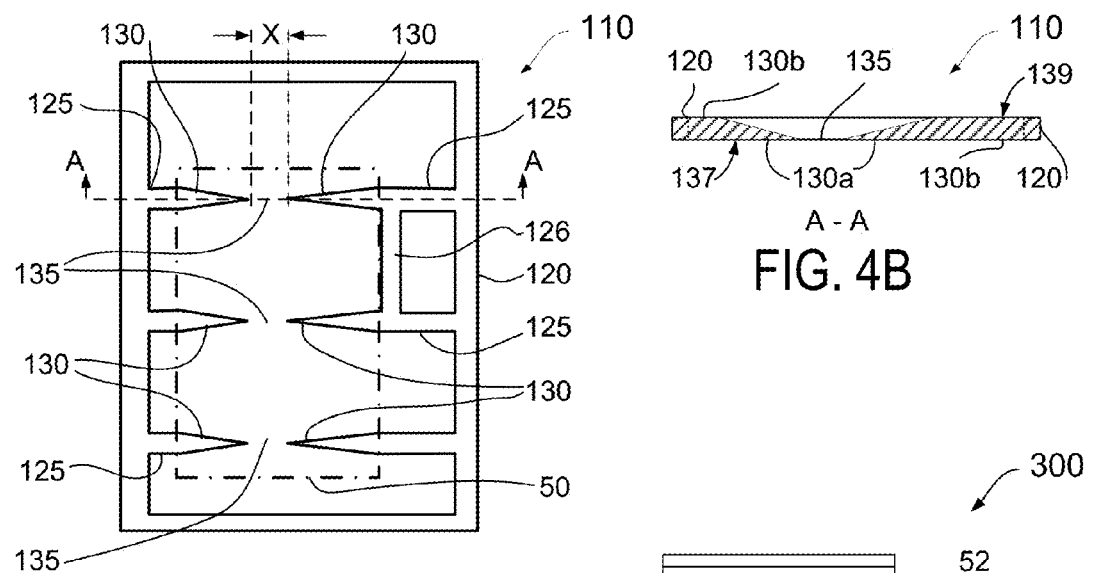
FIG. 4A
FIG. 4B
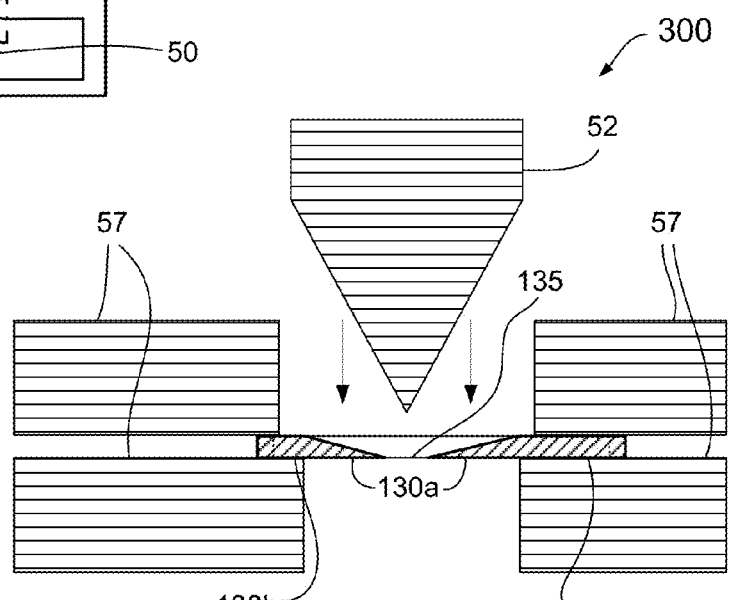
FIG. 5A
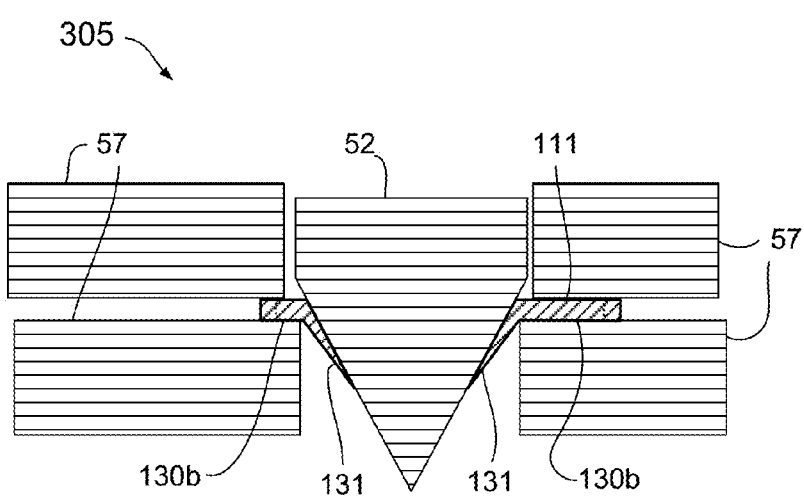
FIG. 5B

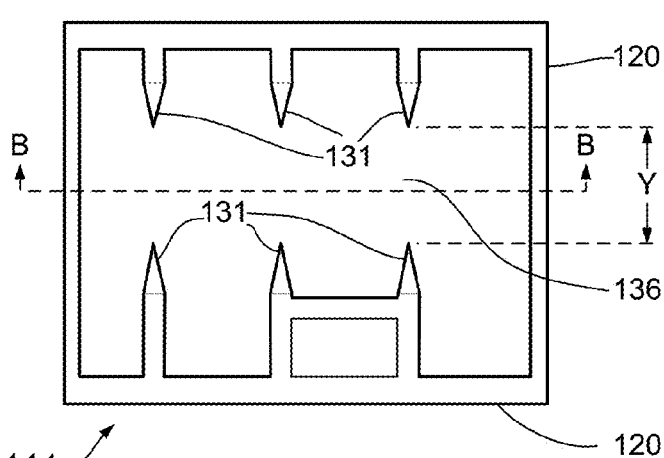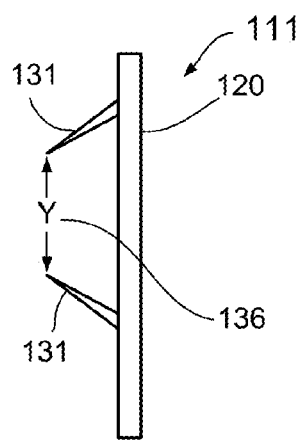
FIG. 6A  FIG. 6B
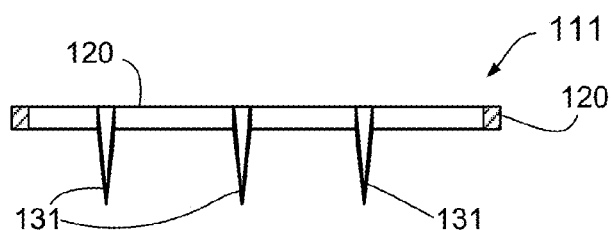
FIG. 6C
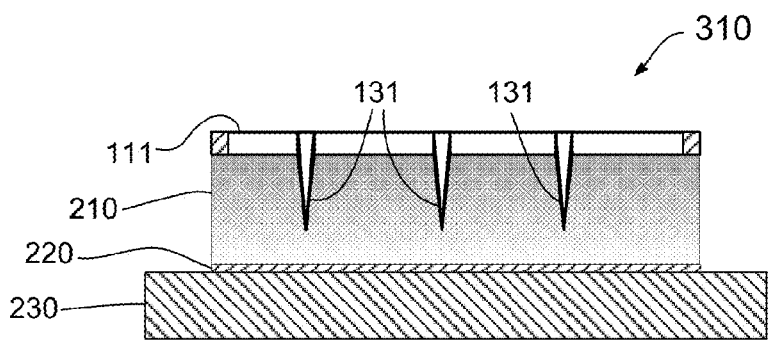
FIG. 7

C - C

D - D

INTEGRATED CIRCUIT MODULE WITH LEAD FRAME MICRO-NEEDLES

RELATED APPLICATIONS

This application is a divisional of U.S. patent application Ser. No. 14/326,842 entitled "An Integrated Circuit Module with Lead Frame Micro-needles" filed Jul. 9, 2014, the entire contents of which are incorporated herein by reference.

BACKGROUND

Wearable medical devices can sometimes include integrated circuitry for collecting sensor data from the patient wearing the device. The resulting medical device tends to be thicker and bulkier than desired for wearing on the patient's body. In addition, costs for such medical device tend to be high due to the varied components and necessary assembly processes. Thus, only patients having the most severe medical conditions warrant the discomfort and costs associated with wearable medical devices.

SUMMARY

In some embodiments, a method of forming an integrated circuit (IC) module with a lead frame micro-needle for a medical device may include forming a lead frame blank including a micro-needle integrally formed therein. The micro-needle may be disposed inward of an outer perimeter of the lead frame blank. The micro-needle may be bent beyond an initial lower side of the lead frame blank. The initial lower side of the lead frame blank may be joined with a protection layer such that the bent micro-needle is embedded in the protection layer. The protection layer may be removably attached to the initial lower side and the bent micro-needle of the lead frame blank. An IC component may be affixed to an upper side of the lead frame blank. In addition, the IC component and at least an upper surface of a core of the lead frame blank may be encapsulated with a molding compound forming a packaging of the IC module. Removal of the protection layer may expose the bent micro-needle projecting away from the packaging.

In some embodiments, the micro-needle may include two opposed micro-needles extending toward one another prior to bending of the two micro-needles beyond the lower side of the lead frame blank. The method may further include sterilizing the lead frame blank before mounting the lead frame blank on the protection layer, such as by applying steam, ethylene oxide, radiation, dry heat, and/or plasma to the lead frame blank. Embodiment methods may further include attaching a substrate to the protection layer, in which a first adhesion strength between the protection layer and the substrate is stronger than a second adhesion strength between the protection layer and the lead frame blank and/or the molding compound, which enables the substrate to be pulled off the packaging with the protection layer remaining attached to the substrate. Embodiment methods may further include pulling the protection layer off the micro-needle and removing an outer frame of the lead frame blank leaving the encapsulated IC component and an inner portion of the lead frame blank.

In some embodiments, the protection layer may be doped with a conductive additive, and the medical device may include a circuit coupled to the conductive additive so that removal of the protection layer activates the IC component.

The medical device may be wearable by a patient, and the IC component may include a sensor coupled to the micro-needle that is configured to sense a parameter when the micro-needle contacts skin of the patient.

Some embodiments include a medical device including an integrated circuit (IC) module coupled to a lead frame including an integrally formed micro-needle. The micro-needle may be formed as a continuous extension of a material forming the lead frame core. The micro-needle may include two opposed micro-needles extending away from the packaging. The IC module may include a lead frame core including an attachment surface and a micro-needle integrally formed therein. The micro-needle may extend beyond a lower planar surface of the lead frame core. An IC component may be conductively bonded to the attachment surface of the lead frame, and a packaging may encapsulate the IC component and at least an upper portion of the lead frame core so that the micro-needle projects outside of the packaging. The IC component may include a sensor coupled to the micro-needle and configured to sense a parameter when the micro-needle contacts skin of a patient wearing the medical device.

In some embodiments, a protection layer may be removably attached to the lower planar surface of the lead frame core, so that at least a tip of the micro-needle is embedded in the protection layer to keep the micro-needle sterile and protect the needle from deformation during storage and handling. Removal of the protection layer may expose the micro-needle projecting away from the packaging. In some embodiments, the protection layer may be removably attached to the lower planar surface of the lead frame core, and a substrate may be secured to the protection layer with an adhesive with a first adhesion strength that is stronger than a second adhesion strength between the protection layer and the lead frame core. The substrate may be pulled off the packaging with the protection layer remaining attached to the substrate. In addition, the protection layer may be removably attached to the lower planar surface of the lead frame core.

In some embodiments, the protection layer may be doped with a conductive additive, and the medical device may include a circuit coupled to the conductive additive and configured so that removal of the protection layer activates the IC component.

BRIEF DESCRIPTION OF THE DRAWINGS

The accompanying drawings are presented to aid in the description of embodiments of the disclosure and are provided solely for illustration of the embodiments and not limitation thereof.

FIG. 1 is a side elevation view of an IC module in accordance with various embodiments.

FIG. 2 is a side elevation view of the IC module of FIG. 1 incorporated into a medical device in accordance with various embodiments.

FIG. 3A illustrates a peel-away substrate on a medical device including an IC module with lead frame micro-needle, in accordance with various embodiments.

FIG. 3B illustrates a medical device including an IC module with lead frame micro-needle being applied to a patient as a medical sensor patch in accordance with various embodiments.

FIG. 3C is a relief perspective view of the medical device of FIG. 3B in accordance with various embodiments.

FIG. 4A is a top plan view of a lead frame blank in accordance with various embodiments.

FIG. 4B is a side elevation cross-sectional view at of the lead frame blank of FIG. 4A, at A-A in accordance with various embodiments.

FIG. 5A is a cross-sectional side elevation view of the lead frame blank of FIG. 4B held in a jig in accordance with various embodiments.

FIG. 5B is a cross-sectional side elevation view of the lead frame blank of FIG. 5A with the micro-needles bent in accordance with various embodiments.

FIG. 6A is a top plan view of the bent lead frame blank of FIG. 5B removed from the jig.

FIG. 6B is a side elevation view of the bent lead frame blank of FIG. 6A.

FIG. 6C is a front elevation cross-sectional view of the bent lead frame blank of FIG. 6A at B-B.

FIG. 7 is a front elevation cross-sectional view of a first stage lead frame assembly in accordance with various embodiments.

DETAILED DESCRIPTION

Figure 8A:
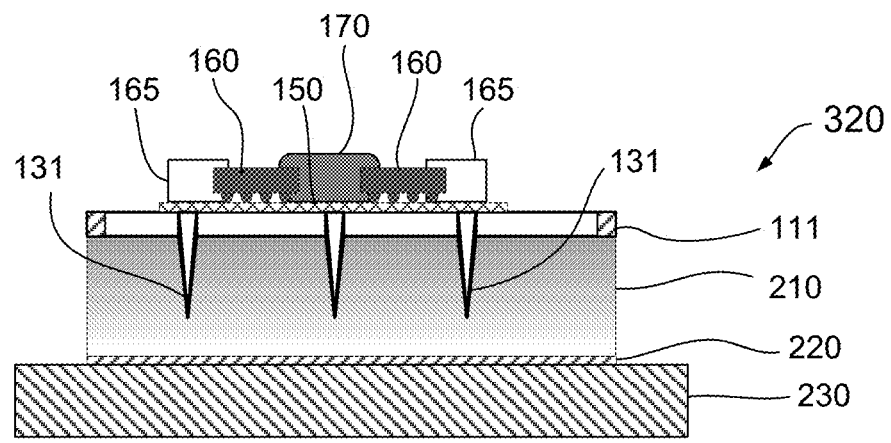
FIG. 8A is a front elevation cross-sectional view of a second stage lead frame assembly in accordance with various embodiments.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the disclosure or the claims. Alternate embodiments may be devised without departing from the scope of the disclosure. Additionally, well-known elements of the disclosure will not be described in detail or will be omitted so as not to obscure the relevant details of the disclosure.

The words "first," "second," "third," and similar terms are used herein for clarity purposes to distinguish various described elements and are not intended to limit the claims to a particular order or hierarchy of elements.

As used herein, the terms "integrated circuit," abbreviated as "IC," or "IC module," refer to a system of circuit elements, including electrical conductors and components, in which all or some of the circuit elements are inseparably associated and electrically interconnected and may be considered indivisible.

As used herein, the term "lead frame," refers to a metal structure inside an IC module that carries signals from the IC components inside the IC module to the outside. The lead frame may be formed from a conductive metal, such as copper, platinum, or gold, as well as combinations of such materials, such as copper coated with gold. In addition, as part of a manufacturing process, the lead frame may be formed from a lead frame blank that includes an inner core and an outer frame. The IC components may be attached directly to the inner core or an intermediate board, and conductively bonded to the inner core using bond wires. The inner core along with an encapsulating molding compound may form a package holding the IC components inside. The outer frame, which may not be encapsulated by the molding compound, may be removed (e.g., cut-off or separated) from the lead frame blank during a manufacturing process.

Various embodiments configure the lead frame of a unitary encapsulated IC module to include integrally formed micro-needles, thereby enabling the manufacture of low cost wearable medical devices with micro-needles. By forming the lead frame so that it includes micro-needles and configuring the IC module with the lead frame at its base, a portion of the lead frame including the micro-needles may remain exposed to an outside surface of the IC module. In this way, the exposed portion of the lead frame including the micro-needles may be used as conductive contact elements for sensors. In particular, the integrally formed micro-needles may remain exposed and project away from the IC module for penetrating the epidermis to reach subcutaneous tissue or the skin generally. The IC module may include a sensor coupled to the micro-needles for recording, measuring, and/or processing various properties. The IC module may include additional IC components, such as a processor, memory, and a battery.

Various embodiments include a method of forming an IC module with a lead frame micro-needle for a medical device. The method may include forming a lead frame blank including one or more micro-needles and bending those micro-needles beyond an initial lower side of the lead frame blank. Prior to affixing IC components, the lead frame blank may be sterilized using techniques that could be harmful to the IC components. Applying a protection layer to at least the sterilized micro-needles may prevent contamination before contact with the skin of the user. Additional IC components may be affixed to the lead frame blank and a molding compound applied to form a unitary IC module packaging. An outer frame of the lead frame blank not contained within the packaging may be removed.

The IC module with lead frame micro-needles of various embodiments may be incorporated into a wearable medical device, such as a medical sensor patch. In addition, the protection layer of the IC module may be removable. In this way the protection layer may keep the micro-needles (or at least the tips of the micro-needles) clean and/or sterilized, and be removed when ready for use. A substrate, such as paper or tape, secured to the protection layer may be used as a peel-away backing for removing the protection layer when appropriate. In addition, conductive properties included in the protection layer may activate certain IC components of the IC module in response to removal of the protection layer.

FIG. 1 illustrates a side elevation cross-sectional view of an IC module 100 with at least one lead frame micro-needle 131, in accordance with various embodiments. The IC module 100 may be formed as a unitary module including a circuit board 150, additional integrated circuits (e.g., semiconductors) 160, a sensor 165, a battery 170, and a lead frame core 112 with micro-needles 131. In this way, various IC components 150, 160, 165, 170 may be integrated into a single microchip-sized device that includes micro-needles 131 integrally formed with the lead frame core 112. The lead frame core 112 may provide support and attachment surfaces for the various IC components 150, 160, 165, 170. The IC components 150, 160, 165, 170 may be encapsulated together, along with at least an upper surface of the lead frame core 112, by a packaging 181 formed from a molding compound. A lower surface of the lead frame core 112, including the micro-needles 131, may not be encapsulated by the packaging 181. The micro-needles 131, which are integrally formed with the lead frame core 112, extend down beyond a lower side of the lead frame core 112 in order to project away from the packaging 181 and be configured to penetrate a patient's skin. Thus the lead frame core 112, or at least the micro-needles 131, may be left exposed to contact from outside the packaging 181, while leaving the other IC components 150, 160, 165, 170 protected by the packaging 181. So configured, when the base of the IC module 100 is placed in contact with the skin of a patient, the micro-needles 131 may directly contact and partially penetrate the skin. A sensor 165 coupled to at least one micro-needle 131 may be configured to sense or measure a parameter (i.e., a characteristic property) of the patient when the micro-needle comes in contact the skin of the patient.

The relative size and shape of the IC module 100, including the individual IC components 150, 160, 165, 170, lead frame core 112 and micro-needles 131, is intended for illustrative purposes only. The size and shape of any of these elements may be modified as part of the design of the IC module 100 to suit a particular or a general purpose. In particular, the micro-needles 131 will typically be much thinner in width in order to penetrate the skin with little or no pain, and be longer or shorter depending upon the depth of penetration appropriate for the particular patch or sensor. Similarly, the configuration of individual components is for illustrative purposes only, and the size and location of components will depend on the particular design. Thus, fewer or more IC components may be included. In addition, the IC module 100 may be designed to include only one micro-needle 131 or numerous micro-needles 131, in accordance with various embodiments FIG. 2 illustrates the IC module 100 of FIG. 1 incorporated into a medical device 200 in accordance with various embodiments. An outer patch structure 240 may be included for aesthetic purposes or to provide additional functional components or properties. For example, while the IC module 100 of FIG. 1 may be used by itself as a medical device, it may be unsightly. Thus, using an outer patch structure 240 may enhance the appearance of the IC module for use as a medical device. Alternatively, a shape of the outer patch structure 240 may be ergonomically formed to fit a particular body part (e.g., shoulder, knee, etc.), simplifying the application and/or removal of the medical device 200 from the patient. As a further example, a larger diameter lower surface 242 of the outer patch structure 240 may include additional adhesive surfaces for sticking to a patient's skin. In addition, the outer patch structure 240 may include one or more optional components 245 appropriate for the particular application or design of the patch. Such optional components 245 may be connected to the lead frame core 112 through optional conductive elements 246.

The outer patch structure 240 may be formed to any size and need not be a unitary homogeneous structure. The outer patch structure 240 may be provided with a pocket, recess, or chamber 247 for receiving the IC module. The outer patch structure 240 may be permanently secured to the IC module 100 or made to be removably secured to the IC module 100. For example, the IC module 100 may be a replaceable or disposable component, while the outer patch structure 240 is intended for extended use in combination with replacement IC modules. Alternatively, the outer patch structure 240 may be configured to be disposable and the IC module 100 may be reusable, in which case the IC module 100 may be inserted into the chamber 247 prior to use and removed for reuse before the outer patch structure 240 is discarded.

FIGS. 3A-3C illustrate an example medical device 200 in various stages of being removed from its protective wrapper for application to a patient. FIG. 3A illustrates the medical device 200 initially being removed from a protective wrapper 250. The protective wrapper 250 may include two opposed covers 251, 252 that sandwich the medical device 200 there between. An individual 10 (e.g., a caregiver or the patient himself) may remove the medical device 200 from the protective wrapper 250 by peeling away the covers 251, 252 one-at-a-time (as illustrated) or alternatively at the same time. In this way, the protective wrapper 250 may be similar to conventional wrappers used for adhesive bandages with gauze. In the process of peeling away the bottom cover 252, a protection layer 211 may be pulled away from the medical device 200 thereby exposing the micro-needles 131.

FIG. 3B illustrates the example medical device 200 being applied by an individual 10 (e.g., a caregiver) to an upper portion of the back of a patient 11 as a medical sensor patch. As illustrated in this FIGS. 3A and 3B, the individual 10 may remove the bottom cover (e.g., 252 in FIG. 3A) to uncover the micro-needles, and firmly place the medical device 200 on the patient 11. The individual 10 may then peel away the top cover 25 as shown in FIG. 3B, leaving only the medical device 200 secured to the patient with the micro-needles 131 penetrating or at least in contact with the skin of the patient 11.

FIG. 3C illustrates the portion of the medical device that contacts the patient showing the micro-needles 131.

The example medical device 200 illustrated in FIG. 3A has a different shape from example medical device 200 illustrated in FIGS. 3B and 3C in order to provide non-limiting examples of how the shapes of such devices may vary.

FIGS. 4A-4B illustrate an example of lead frame blank 110 that may be used to form an IC module in accordance with various embodiments. FIG. 4A illustrates a top plan view of the lead frame blank 110, while FIG. 4B illustrates a side elevation cross-sectional view of the lead frame blank 110 of FIG. 4A, at A-A. The lead frame blank 110 may be formed by stamping, pressing, etching, or any other suitable techniques for forming lead frames for electronic circuits. The lead frame blank 110 may be formed from a pliable conductive material, such as but not limited to copper. The lead frame blank 110 may be formed in various shapes and sizes; the rectangular shape shown in FIGS. 4A and 4B is for illustrative purposes only.

Referring to the FIG. 4A, the lead frame blank 110 may include an outer frame 120, inner leads 125, inner lands 126, and one or more integrally formed pre-bent micro-needles 130. The outer frame 120 may extend around an entire perimeter of the lead frame blank 110. Although the outer frame 120 is shown as a continuous element, it may have breaks, discontinuities or other variations in form Inner leads 125 may connect the innermost portions of the lead frame blank 110 to the outer frame 120. The inner lands 126 may support or connect to IC components or other structures attached thereon, such as an IC board Inner portions of the inner leads 125 may also act like inner lands 126 for supporting or connecting to IC components or structures as an attachment surface.

The pre-bent micro-needles 130 may be formed inward of an outer perimeter of the lead frame blank 110, as a continuous extension of a material forming the lead frame blank 110.

In this way, the pre-bent micro-needles 130 may be integrally formed as an unbroken extension (i.e., without interruption) of one or more other lead frame elements (e.g., outer frame 120, inner leads 125, or inner lands 126). In addition, the pre-bent micro-needles 130 may be sharpened to a point or formed thin and pointy enough to penetrate skin. For example, if very sharp micro-needles are desired, the pre-bent micro-needles 130 may be etched to form tiny needle like structures (i.e., cylindrical forms ending in a point) or triangular projections. The tips of the pre-bent micro-needles 130 (or at least one tip) may be coated with biologically compatible conductive layer, such as platinum. The embodiment illustrated in FIG. 4A includes six pre-bent micro-needles 130, which are grouped into three pairs. The pairs of pre-bent micro-needles 130 include two opposed pre-bent micro-needles 130 extending toward one another. The endpoints of the paired pre-bent micro-needles 130 are spaced apart by a distance X, which forms a gap 135, which may be sized to meet various functional and/or structural requirements. Alternatively, the gap 135 may be eliminated, so that the endpoints touch or even join in the center. At a later stage in the process flow of forming the IC module illustrated FIGS. 5A and 5B, the pre-bent micro-needles 130 are bent to an orientation appropriate for penetrating skin, such as using a press tool (the outline of which is indicated at 50 in FIG. 4A).

Referring to FIG. 4B, the pre-bent micro-needles 130 may include micro-needle inner portions 130a closest to the gap 135 and micro-needle outer portions 130b closest to the outer frame 120. In this embodiment, the pre-bent micro-needles 130 are tapered, with a thicker part at the micro-needle outer portion 130b tapering to a point at the end of the micro-needle inner portion 130a. The taper is also illustrated as extending from an initial upper side 139 to an initial lower side 137 of the pre-bent micro-needles 130. Alternatively, the taper may meet in the middle between the lower and upper sides 137, 139, or taper in the opposite direction (i.e., being thickest at the lower side 137 and tapering toward a point at the upper side 139).

FIGS. 5A and 5B illustrate two steps of an embodiment method of bending the pre-bent micro-needles 130. FIG. 5A illustrates a cross-sectional side elevation view of the lead frame blank 110 held in a jig 57 for bending micro-needles. Above the lead frame blank 110 is a pressing tool 52 (the outline of which is denoted as 50 in FIG. 4A). The micro-needles 130 may be bent by moving the pressing tool 52 through the gap 135 as indicated by the arrows in FIG. 5A to the final position illustrated in FIG. 5B. As the pressing tool 52 continues moving downwards through the gap 135, its angled edges engage the upper surfaces of the micro-needle inner portions 130a bending them down. The pressing tool 52 may be designed to bend the micro-needle inner portions 130a beyond a lower planar surface (e.g., lower side 137 of FIG. 4B) of the lead frame blank 110, less than 90° to form bent micro-needles 131 (which is referred to herein as a bent lead frame blank 111). An angle of the bent micro-needles 131 may be greater or less than that shown. For example, the bent micro-needles 131 may be bent less than that shown (i.e., still pointing toward one another), may be bent more so they are approximately perpendicular to the planer portions of the bent lead frame blank 111 (i.e., pointing parallel to one another), or bent past a perpendicular orientation (i.e., pointing outwardly from one another).

FIGS. 6A-6C illustrate various views of the bent lead frame blank 111 of FIG. 5B. In particular, FIG. 6A illustrates a top plan view and FIG. 6B illustrates a side elevation view of the bent lead frame blank 111. FIG. 6C illustrates a front elevation cross-sectional view of the bent lead frame blank of FIG. 6A, at B-B. Although the outer frame 120 is generally unchanged, the tips of the pairs of bent micro-needles 131 are further separated apart by distance Y, presenting a wider gap 136 between them.

Once the bent lead frame blank 111 is formed, it may be subjected to one or more cleaning and/or sterilization operations, particularly for sterilizing the micro-needles 131 that may contact and penetrate a patient's skin. Medical devices intended to penetrate the skin during use should be well cleaned and sterilized to avoid exposing a patient to harmful chemicals or metals and to prevent infection. Numerous sterilization techniques may be used, including steam, ethylene oxide, radiation, dry heat, or plasma that are known to be effective in sterilizing needles and similar medical devices. An advantage of sterilizing the bent lead frame blank 111 at this point is that no electronic components have yet been attached. Attaching electronic components before sterilization may limit the types of sterilization techniques that can be used to those that will not damage integrated circuits, as well as add expense to the sterilization process because of the extra care involved in handling the attached electronic components. Optionally, the bent micro-needles 131 or other portions of the lower side (e.g., 137 in FIG. 4B) intended to contact a patient's skin may be additionally treated at this stage. For example, additional sterilization, a coating for biocompatibility/drug delivery, or other finishes may be applied to the bent micro-needles 131 or other portions of the lower side. For example, antimicrobial or antibiotic coatings may be applied for subcutaneous application.

FIG. 7 illustrates the bent lead frame blank 111 of FIG. 6C joined with other layers to form a first stage lead frame assembly 310 in accordance with various embodiments. The first stage lead frame assembly 310 may be assembled by a process of joining the various layers. A process of joining the various layers may bring the bent lead frame blank 111 into contact with a stationary protection layer 210, the stationary protection layer 210 into contact with the bent lead frame blank 111, or the two elements 111, 210 may both be moved toward one another. In this embodiment, the process of joining the various layers embeds the bent lead frame blank 111, and particularly the bent micro-needles 131, into the protection layer 210. The protection layer 210 may maintain the sterilized condition of the bent micro-needles 131. In addition, the protection layer 210 may eventually help prevent a patient or caregiver from unintentionally sticking themselves or others with the bent micro-needles 131. The protection layer 210 may also protect the micro-needles 131 from being bent during later manufacturing steps or handling and packaging.

The protection layer 210 may be supported by a carrier 230. The carrier 230 may be a rigid support surface, such as glass or ceramic, or a removable substrate, such as paper, fabric, or tape, supported by another subsurface (not shown). A joining layer 220 may join the carrier 230 to the protection layer 210. The joining layer 220 may be an adhesive layer used to hold the protection layer 210 to the carrier 230 when the carrier 230 is subsequently removed. Alternatively, the joining layer 220 may be a release layer for encouraging the carrier 230 to easily separate from the protection layer 210.

The protection layer 210 may be formed of an acrylic rubber or silicone, with additives for balancing the adhesion strength. In this way the protection layer 210 may have a low adhesion property, enabling it to gently stick to the bent lead frame blank 111, while being able to be removed later (i.e., demounting). In addition, the protection layer 210 may be initially applied in a softened state, so that the bent micro-needles 131 may be embedded therein, and later hardened through chemical or thermal treatments. The protection layer 210 need not be rigid but may have a high enough compression strength to support the bent lead frame blank on its own. The protection layer 210 may be formed of a thermoplastic, such as a non-photodefinable polyimide adhesive (e.g., HD-3007 series materials from Hitachi DuPOnt (HD) Micro-Systems™, Cupertino, Calif.), or a UV curable polymer, such as a structural adhesive (e.g., 3M™ Scotch-Weld™ Structural Plastic Adhesive DP8010, 3M, St. Paul, Minn.).

Figure 8B:
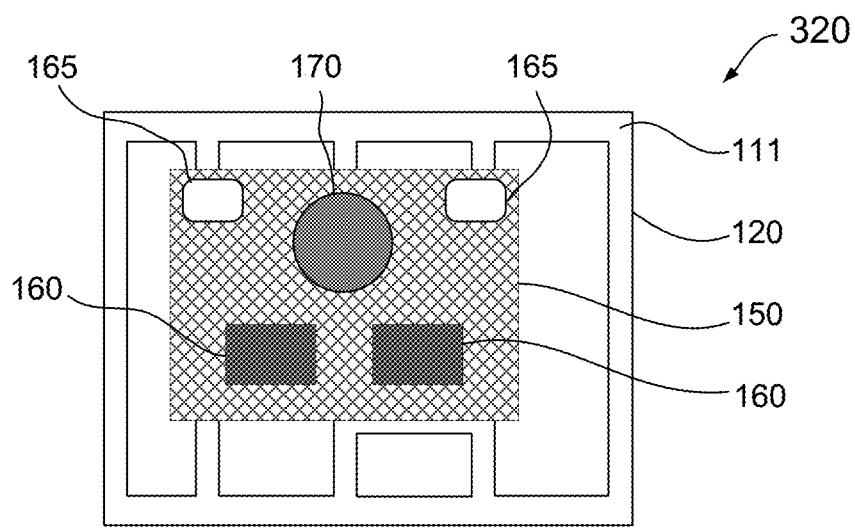
FIG. 8B is a top view of the second stage lead frame assembly of FIG. 8A.

FIGS. 8A and 8b illustrate different views of a second stage lead frame assembly 320 in accordance with various embodiments. In particular, FIG. 8A illustrates a front elevation cross-sectional view similar to the first stage lead frame assembly of FIG. 7, but with additional elements attached thereto. FIG. 8B illustrates a top view of the bent lead frame assembly of FIG. 8A. The order of particular components/elements added may vary depending on the design and desired configuration of the eventual IC module.

A circuit (e.g., IC) board 150 may be one of the initial elements affixed to form the second stage lead frame assembly 320. The circuit board 150 may be a sturdy flame-resistant material, such as a glass-reinforced epoxy laminate sheet (e.g., an FR-4 grade printed circuit board). The circuit board 150 may be secured with an adhesive to lands of the bent lead frame blank 111 (e.g., 125, 126 in FIG. 4A). Other elements, such as one or more integrated circuits 160, one or more sensors 165, and a battery 170 may also be added. The integrated circuits 160 are semiconductors designed and formed to provide a given circuit function. Each integrated circuit 160 may include a set of electronic circuits on one small plate ("chip") of semiconductor material, normally silicon, which may be made much smaller than a discrete circuit made from independent components. The integrated circuits 160 may be affixed to the circuit board 150 using thermal conductive adhesives. Fewer or additional integrated circuits 160 may be affixed to form the second stage lead frame assembly 320. In addition, passives and other elements may be added. For example, more than one sensor 165 may be included. The sensors 165 may be redundant or measure different properties. In addition, the battery 170 may supply power to the various IC components. The battery 170 may be a button-cell battery suited to the various IC components that might use it.

Optionally, the IC components may include a special purpose processor for handling data collected by sensors. Additionally, components such as a transceiver, or at least a transmitter, may be included in order to transmit information collected and/or receive commands related to the medical device. In addition, other elements such as a communication or power supply port may be included.

Figure 9A:
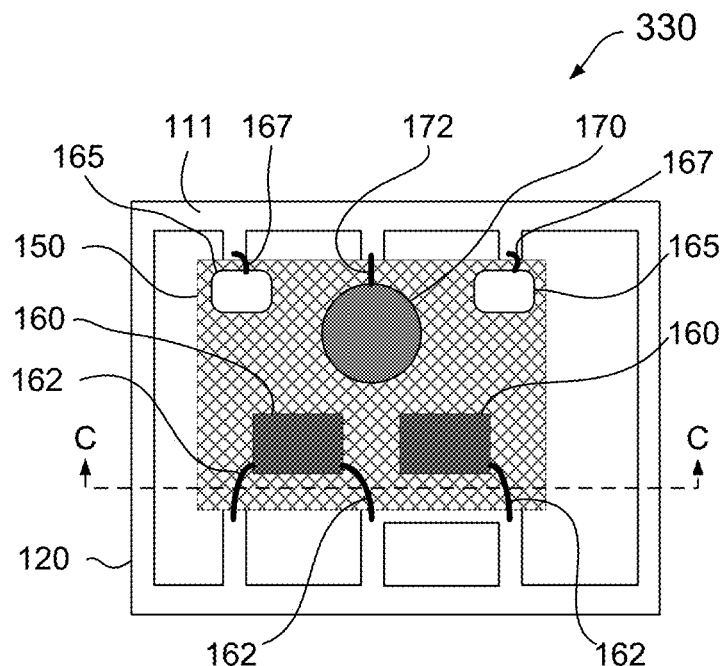
FIG. 9A is a top view of a third stage lead frame assembly in accordance with various embodiments.
Figure 9B:
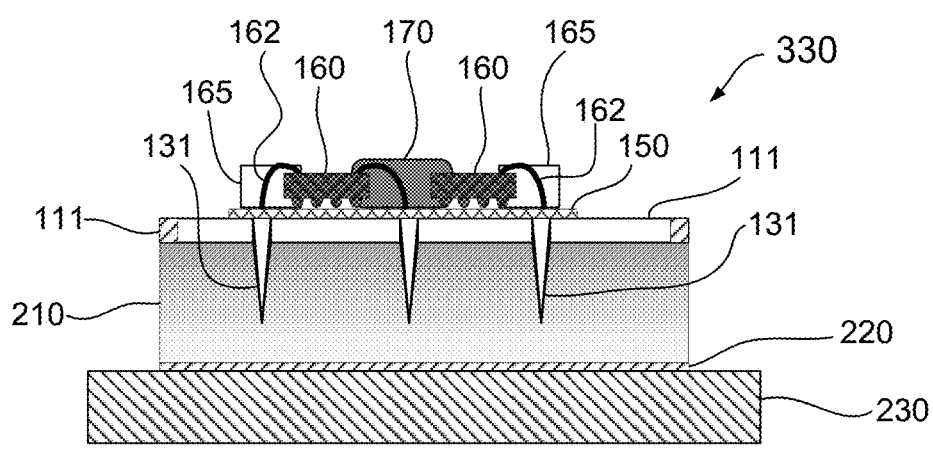
FIG. 9B is a front elevation cross-sectional view of the third stage lead frame assembly of FIG. 9A at C-C.

FIGS. 9A and 9B illustrate different views of a third stage lead frame assembly 330, in accordance with various embodiments. In particular, FIG. 9A illustrates a top view similar to the second stage lead frame assembly 320 of FIGS. 8A and 8B, but with the various IC components wire-bonding to the bent lead frame blank 111. FIG. 9B illustrates a front elevation cross-sectional view of the third stage lead frame assembly 330 of FIG. 9A, at C-C. The wire-bonding may connect the individual IC components 160, 165, 170 to the bent lead frame blank 111, providing an electrical connection. For example, first conductive wires 162 may connect the integrated circuits 160 to a first portion of the bent lead frame blank 111, second conductive wires 172 may connect the battery 170 to a second portion of the bent lead frame blank 111, and third conductive wires 167 may connect the sensors 165 to a third portion of the bent lead frame blank 111. The conductive wires 162, 167, 172 may be gold or other material used for providing reliable electrical conductivity between the bent lead frame blank 111 and the respective components 160, 165, 170. The first, second, and third portions of the bent lead frame blank 111 to which the conductive wires 162, 167, 172 are attached may be portions of the leads or lands (e.g., 125, 126 in FIG. 4A) of the bent lead frame blank 111.

Figure 10:
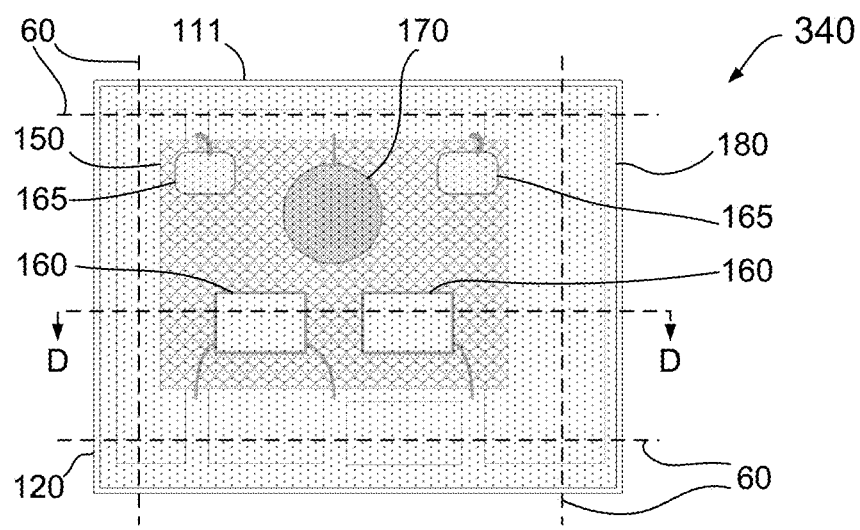
FIG. 10 is a top plan view of a fourth stage lead frame assembly in accordance with various embodiments.

FIG. 10 illustrates a top plan view of a fourth stage lead frame assembly 340, in accordance with various embodiments. FIG. 10 is similar to the view of the third stage lead frame assembly 330 of FIG. 9A, but with a molding compound 180 added. The molding compound 180 encapsulates the IC components 150, 160, 165, 170 and may encapsulate portions of the bent lead frame blank 111. The molding compound 180 may be applied by various methods, such as injection molding, transfer molding, and other techniques. Once hardened, the molding compound 180 may support and encase the IC components 150, 160, 165, 170, preventing physical damage and corrosion. The hardened molding compound 180 forms a packaging of the IC module. The molding compound 180 may be in epoxy plastic suited to provide adequate protection of the IC components 150, 160, 165, 170 and support for the bent micro-needles 131 projecting outside and away from the packaging. Optionally, openings or windows (not shown) may be formed in the packaging for elements such as light emitters, sensors and/or switches.

Once the molding compound 180 is hardened or at least semi-hardened, the third stage lead frame assembly 330 may be trimmed. The cut lines 60 indicate where the third stage lead frame assembly 330 may be trimmed. Such trimming may not only reduce the size of the third stage lead frame assembly 330 but also remove the outer frame 120 of the bent lead frame blank 111. Removal of the outer frame 120 leaves the encapsulated IC components 150, 160, 165, 170 and inner lead frame portions. The hardened and trimmed molding compound 180 may be the intended packaging for the final IC module (e.g., 100 in FIG. 1).

Figure 11:
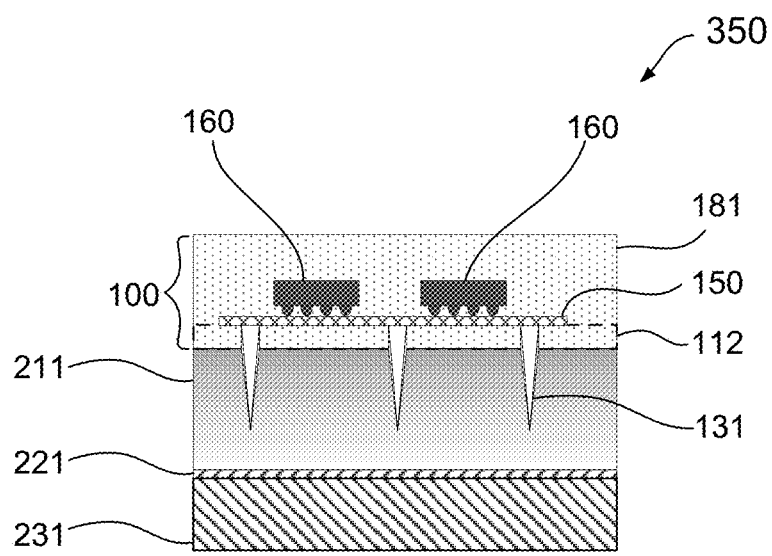
FIG. 11 is a rear elevation cross-sectional view of an IC module with lead frame micro-needles in accordance with various embodiments.

FIG. 11 illustrates a rear elevation cross-sectional view of a fifth stage lead frame assembly 350, in accordance with various embodiments. FIG. 11 is a cross-sectional view of an IC module 100 with lead frame micro-needles at cross section D-D in FIG. 10 after the trimming at cut lines 60, in accordance with various embodiments. The trimmed assembly now includes the IC module 108, trimmed protection layer 211, the trimmed joining layer 221, and the trimmed carrier layer 231. The trimmed joining layer 221 and the trimmed carrier layer 231 are optional and may not be used in designs using a more hard trimmed joining layer 221. At this stage, the lead frame assembly 350 may be tested using conventional IC testing techniques. Optionally, the trimmed joining layer 211 may be removed for testing the micro-needles 131. After such testing, a replacement protection layer may be added over the micro-needles 131. The trimmed joining layer 211 may serve to protect the tips of the micro-needles 131 embedded therein from bending, poking people, and being contaminated. In some embodiments, the tips of the micro-needles 131 may need to remain clean and hygienic enough for medical purposes.

Figure 12A:
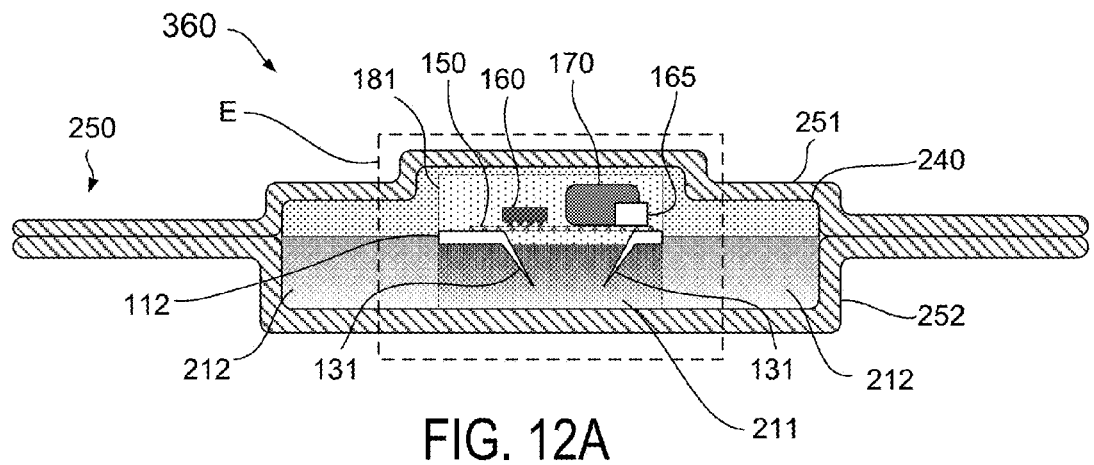
FIG. 12A is a side elevation cross-sectional view of an IC module with lead frame micro-needles in a medical device wrapped in a removable wrapper in accordance with various embodiments.
Figure 12B:
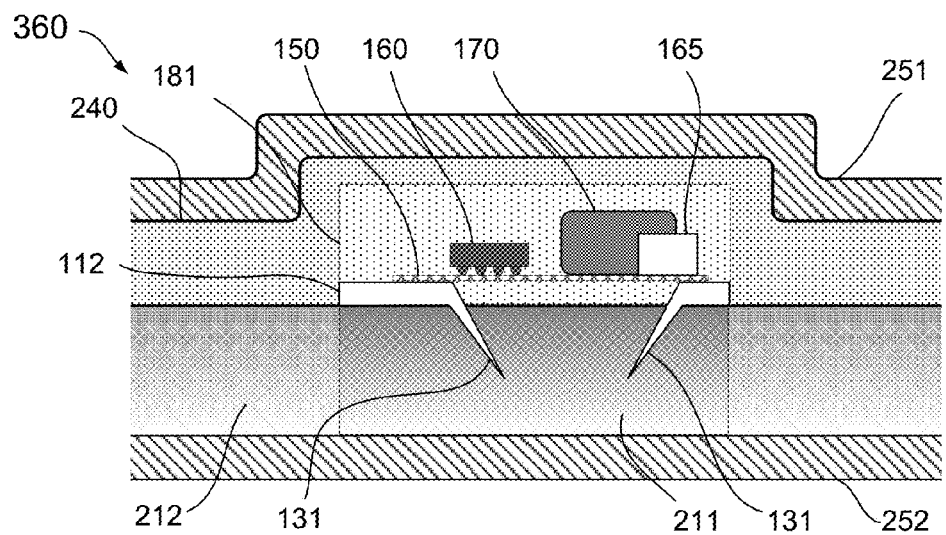
FIG. 12B is a relief view of the IC module with lead frame micro-needles of FIG. 12A, at E.

FIGS. 12A and 12B illustrate an IC module with lead frame micro-needles implemented in a medical device wrapped in a removable substrate, in accordance with various embodiments. In particular, FIG. 12A illustrates a cross-sectional view of the IC module 100 of FIG. 1, in a outer patch structure 240 wrapped in a removable wrapper 250. FIG. 12B is a detail view of the IC module with lead frame micro-needles of FIG. 12A, at E. Application of the wrapper 250 may form a final stage assembly 360. The wrapper 250 may be formed from two opposed covers 251, 252 enveloping the outer patch structure 240 and protection layers 211, 212 within. In the embodiment of FIGS. 12A and 12B, the trimmed protection layer 211 and trimmed carrier layer 231 (FIG. 11) are either not included or have been removed prior to wrapping. In addition, a peripheral protection layer 212 may be added for support. Optionally, the peripheral protection layer 212 need not be included or may have a tapered profile to reduce the size of the final stage assembly 360. The wrapper 250 may be added using traditional patch technology web conversion techniques.

Figure 13:
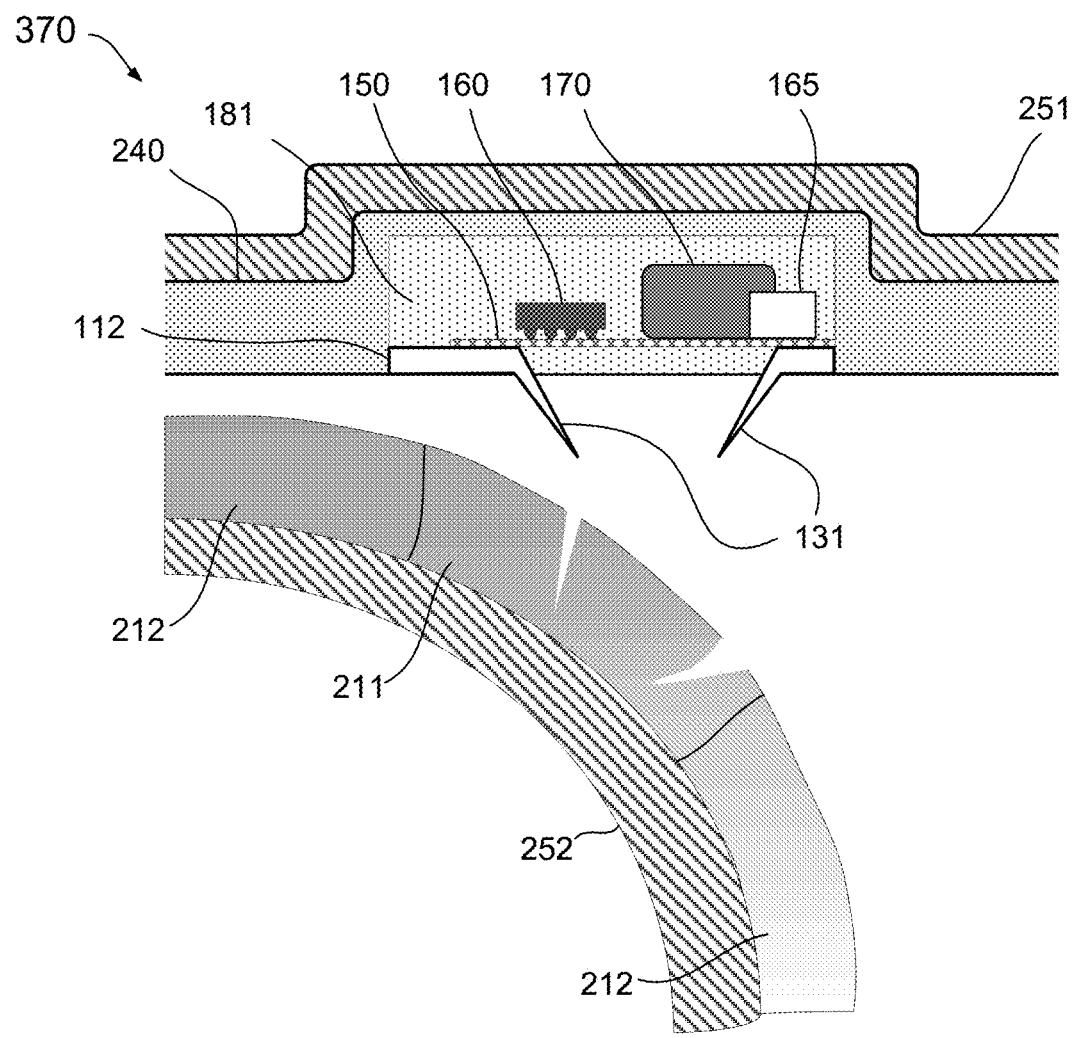
FIG. 13 is a side elevation cross-sectional view of the medical device of FIG. 12B with a peel-away substrate being removed in accordance with various embodiments.

FIG. 13 illustrates a final stage assembly of FIG. 12B with the bottom wrapper cover 252 being pulled away, pulling with it the protection layers 211, 212 during the opening stage 370 of the wrapper in accordance with various embodiments. The bottom wrapper cover 252 may be peeled off just before applying the medical device 200 to a patient. The opening stage 370 may include peeling away at least one of the two opposed wrapper covers 251, 252. The adhesive between the bottom wrapper cover 252 and the protection layers 211, 212 may have a first adhesion strength that is stronger than a second adhesion strength between the protection layers 211, 212 and the lower components of the outer patch structure 240. Those lower components may include the underside of the outer patch structure 240, portions of the trimmed lead frame core 112, portions of the trimmed packaging 181, and the micro-needles 131.

The trimmed protection layer 211, which protects the micro-needles 131, may be doped with a conductive additive (i.e., a conductive doping), such as silver (Ag). The conductive doping may make the trimmed protection layer 211 conductive. The IC module may be designed to detect when the protection layer is removed, which may be used to trigger the activation of other elements of the IC module. For example, the doped adhesive may maintain a closed-circuit of the IC components, which upon opening by removal of the protection layer will activate other IC components or functions. When the doped protection layer has been removed, the micro-needles 131 are exposed and the device is ready to be applied to a patient's skin.

Figure 14:
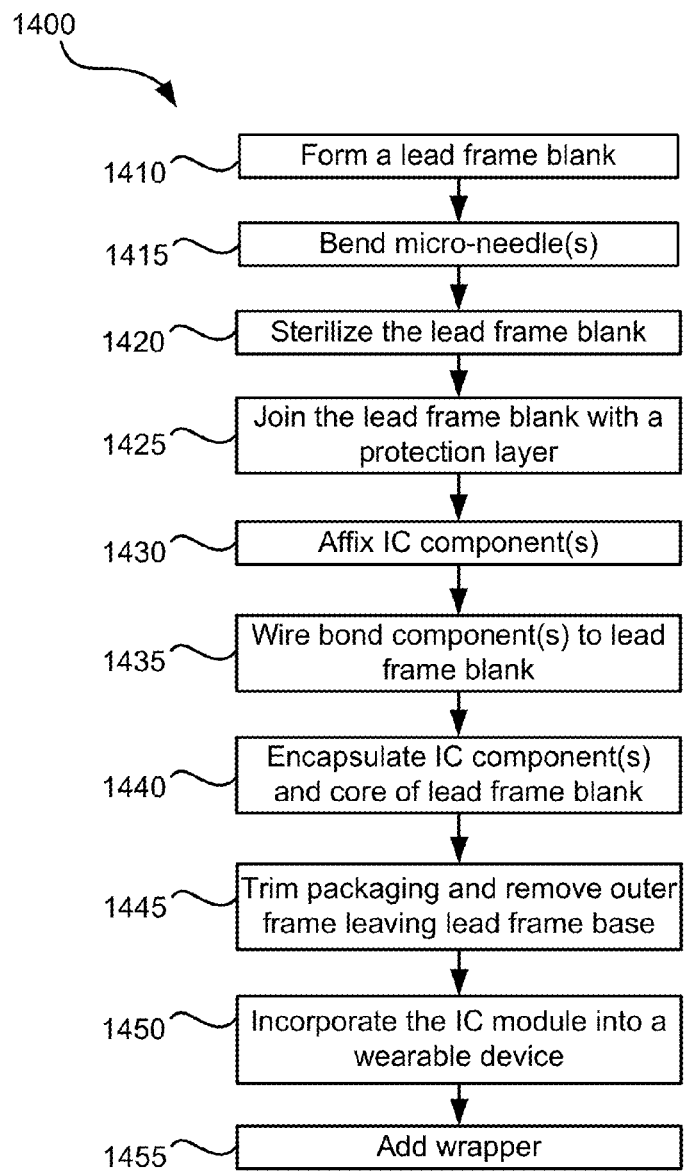
FIG. 14 is a process flow diagram illustrating an embodiment method of forming the medical device of FIG. 1.

FIG. 14 illustrates an embodiment method 1400 of forming the medical device of FIG. 1, in accordance with various embodiments. In block 1410, a lead frame blank may be formed using any known method for forming lead frames.

In block 1415, the lead frame blank may be bent to form the micro-needles, such as described with reference to FIGS. 5A-5B.

In block 1420, the lead frame blank may be cleaned and sterilized. Sterilization process may include cleaning and applying more than one stage of sterilization treatments to the bent lead frame blank. As described above, sterilization techniques such as the application of steam, ethylene oxide, radiation, dry heat or plasma may be used.

In block 1425, the lead frame blank may be joined with a protection layer. For example, an initial lower side of the lead frame blank may be joined with the protection layer such that the bent micro-needles are embedded in the protection layer. This protection layer may be removably attached to that initial lower side of the lead frame blank and the micro-needles. For example, the process described with reference to FIG. 7 may be used for adding the protection layer to the lead frame blank.

In block 1430, one or more IC components may be affixed to an upper side of the lead frame blank. Affixing the IC components may include securing the IC components to the lead frame blank, and coupling components to one another. For example, the process described with reference to FIGS. 8A-8B may be used to affix the IC components to the lead frame blank.

In block 1435, the IC components may be wire bonded to the lead frame blank. For example, the process described with described to FIGS. 9A-9B may be used to wire bond the IC components to the lead frame blank.

In block 1440, the IC components and at least an upper surface of a core of the lead frame blank may be encapsulated with a molding compound. This encapsulation may form a packaging of the IC module. For example, the process described with reference to FIG. 10 may be used to encapsulate the one or more IC components and a portion of the lead frame blank.

In block 1445, the packaging of the IC module may be trimmed, which may remove an outer frame of the lead frame blank. Removing the outer frame of the lead frame blank may leave the encapsulated IC component(s) and inner portions of the lead frame blank to form the IC module. For example, the process described with reference to FIGS. 10-11 may be used to trim the assembly and the packaging of the IC module.

In block 1450, the IC module may be incorporated into a wearable device, such as in medical sensor patch. For example, the IC module may be inserted into a medical patch structure, such as that described with reference to FIG. 2.

In block 1455, the medical device may be enveloped in a removable wrapper. For example, the wrapper described with reference to FIG. 12A may be applied to the medical device. The wrapper may be the final outer packaging used to deliver the medical device to medical providers and/or patients.

Figure 15:
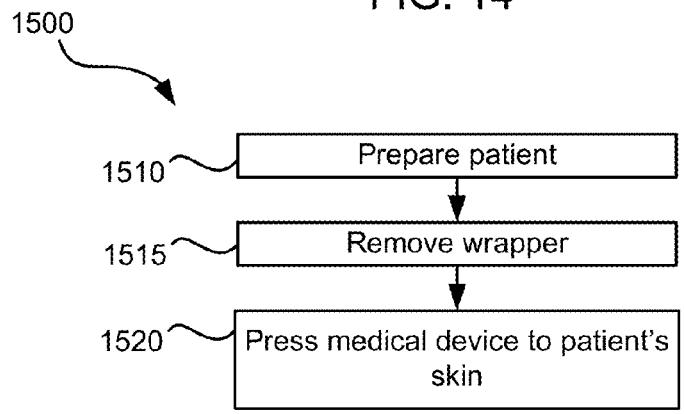
FIG. 15 is a process flow diagram illustrating an embodiment method of applying the medical device of FIG. 12A to a patient.

FIG. 15 illustrates an embodiment method 1500 of applying the medical device of FIG. 12A to a patient, in accordance with various embodiments. In block 1510, the patient may be prepared for receiving medical device. Preparation may include pulling away a removing clothes, cleaning the skin, and generally clearing the area where the medical device will be applied. In block 1515, the wrapper enveloping the medical device may be removed. For example, the process described with reference to FIGS. 3A-3C and 13 may be applied to remove the wrapper. As described above with reference to FIG. 13, the wrapper may be removable so that it also removes the protective layer covering the micro-needles 131. In block 1520, the medical device may be pressed against the patient's skin. An adhesive on the underside of the medical device may hold the medical device in place. In addition, pressing the medical device against the patient's skin may cause the micro-needles 131 to penetrate the patient's skin. In this way, sensors of the medical device coupled to the micro-needles may take appropriate measurements.

Any reference to claim elements in the singular, for example, using the articles "a," "an" or "the" is not to be construed as limiting the element to the singular.

One skilled in the relevant art will recognize that many possible modifications and combinations of the aspects of the disclosed embodiments may be used, while still employing the same basic underlying mechanisms and methodologies. The foregoing description, for purposes of explanation, has been written with references to specific embodiments. However, the illustrative discussions above are not intended to be exhaustive or to limit the disclosure to the precise forms disclosed. Many modifications and variations are possible in view of the above teachings. The embodiments were chosen and described to explain the principles of the disclosure and their practical applications, and to enable others skilled in the art to best utilize the disclosure and various embodiments with various modifications as suited to the particular use contemplated. Thus, the present disclosure is not intended to be limited to the embodiments and individual aspects of the disclosed technologies shown and described herein, but is to be accorded the widest scope consistent with the following claims and the principles and novel features disclosed herein.

What is claimed is:

1. A method of forming an integrated circuit (IC) module with a lead frame micro-needle for a medical device, comprising:
   forming a lead frame blank including a micro-needle integrally formed therein, the micro-needle disposed inward of an outer perimeter of the lead frame blank;
   bending the micro-needle beyond an initial lower side of the lead frame blank;
   joining the initial lower side of the lead frame blank with a protection layer such that the bent micro-needle is embedded in the protection layer, wherein the protection layer is removably attached to the initial lower side and the bent micro-needle of the lead frame blank;
   affixing an IC component to an upper side of the lead frame blank; and
   encapsulating the IC component and at least an upper surface of a core of the lead frame blank with a molding compound forming a packaging of the IC module, wherein removal of the protection layer exposes the bent micro-needle projecting away from the packaging.

2. The method of claim 1, wherein the micro-needle includes two opposed micro-needles extending toward one another prior to the bending of the two opposed micro-needles beyond the initial lower side of the lead frame blank.

3. The method of claim 1, further comprising:
   sterilizing the lead frame blank before mounting the lead frame blank on the protection layer.

4. The method of claim 3, wherein the sterilizing the lead frame blank includes applying at least one member of the group consisting of steam, ethylene oxide, radiation, dry heat, and plasma to the lead frame blank.

5. The method of claim 1, further comprising:
   attaching a substrate to the protection layer, wherein a first adhesion strength between the protection layer and the substrate is stronger than a second adhesion strength between the protection layer and at least one of the lead frame blank, the molding compound, or combinations thereof.

6. The method of claim 5, wherein the substrate may be pulled off the packaging with the protection layer remaining attached to the substrate.

7. The method of claim 1, wherein a substrate may be pulled off the packaging such that the protection layer is also pulled off the micro-needle.

8. The method of claim 1, wherein the protection layer is doped with a conductive additive and the medical device includes a circuit coupled to the conductive additive when the medical device is assembled and configured so that the removal of the protection layer activates the IC component.

9. The method of claim 1, wherein the medical device is wearable by a patient, and wherein the IC component includes a sensor coupled to the micro-needle that is configured to sense a parameter when the micro-needle contacts skin of the patient.

10. The method of claim 1, further comprising:
    removing an outer frame of the lead frame blank leaving the encapsulated IC component and an inner portion of the lead frame blank.

\* \* \* \* \*